(12) United States Patent
Torashima et al.

(10) Patent No.: US 10,293,374 B2
(45) Date of Patent: May 21, 2019

(54) CAPACITIVE TRANSDUCER AND METHOD OF MANUFACTURING SAME

(71) Applicant: CANON KABUSHIKI KAISHA, Tokyo (JP)

(72) Inventors: Kazutoshi Torashima, Yokohama (JP); Kenichi Nagae, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 175 days.

(21) Appl. No.: 14/251,743

(22) Filed: Apr. 14, 2014

(65) Prior Publication Data

US 2014/0318255 A1    Oct. 30, 2014

(30) Foreign Application Priority Data

Apr. 25, 2013  (JP) ................ 2013-092668
Feb. 7, 2014   (JP) ................ 2014-022479

(51) Int. Cl.
 H04R 19/00    (2006.01)
 B06B 1/02     (2006.01)
 G01N 29/24    (2006.01)
 G01N 29/34    (2006.01)

(52) U.S. Cl.
 CPC ....... B06B 1/0292 (2013.01); G01N 29/2406 (2013.01); G01N 29/2418 (2013.01); G01N 29/34 (2013.01); *G01N 2291/045* (2013.01); *G01N 2291/101* (2013.01); *Y10T 29/49007* (2015.01)

(58) Field of Classification Search
 USPC .......................................................... 340/73
 See application file for complete search history.

(56) References Cited

U.S. PATENT DOCUMENTS

| | | | |
|---|---|---|---|
| 2,837,728 A | 6/1958 | Schuck | 367/153 |
| 4,425,525 A | 1/1984 | Smith et al. | 310/336 |
| 4,460,841 A | 7/1984 | Smith et al. | 310/334 |
| 5,488,956 A | 2/1996 | Bartelt et al. | 600/459 |
| 5,870,351 A * | 2/1999 | Ladabaum | B06B 1/0292 367/163 |
| 6,359,367 B1 | 3/2002 | Sumanaweera et al. | 310/309 |

(Continued)

FOREIGN PATENT DOCUMENTS

| | | |
|---|---|---|
| CN | 101883309 | 11/2010 |
| CN | 102015127 | 4/2011 |

(Continued)

OTHER PUBLICATIONS

Drinkwater, Bruce W., and Paul D. Wilcox. "Ultrasonic arrays for non-destructive evaluation: A review." Ndt & E International 39.7 (2006): 525-541.*

(Continued)

*Primary Examiner* — Isam A Alsomiri
*Assistant Examiner* — Jonathan D Armstrong
(74) *Attorney, Agent, or Firm* — Venable LLP

(57) ABSTRACT

Provided is a capacitive transducer including an element including a plurality of cells supported such that a vibrating membrane including one of a pair of electrodes formed with an gap inbetween is capable of vibration, wherein a distance between a pair of electrodes of a cell in an end portion of the element is greater than that between a pair of electrodes of a cell in a middle portion of the element.

7 Claims, 4 Drawing Sheets

(56) References Cited

U.S. PATENT DOCUMENTS

| | | | |
|---|---|---|---|
| 6,381,197 B1* | 4/2002 | Savord | B06B 1/0292 367/178 |
| 7,778,113 B2 | 8/2010 | Machida et al. | 367/181 |
| 7,892,176 B2* | 2/2011 | Wodnicki | A61B 8/0833 257/E27.006 |
| 8,456,958 B2 | 6/2013 | Felix et al. | 367/181 |
| 2005/0075572 A1 | 4/2005 | Mills et al. | 600/459 |
| 2007/0059858 A1 | 3/2007 | Caronti et al. | 438/50 |
| 2008/0259725 A1 | 10/2008 | Bayram et al. | 367/7 |
| 2010/0283354 A1 | 11/2010 | Soeda | 310/300 |
| 2010/0327380 A1 | 12/2010 | Chang | 257/419 |
| 2011/0060255 A1* | 3/2011 | Chen | B06B 1/0292 601/2 |
| 2011/0208059 A1 | 8/2011 | Cerofolini | 600/447 |
| 2012/0150012 A1 | 6/2012 | Fujimoto et al. | |
| 2012/0259218 A1 | 10/2012 | Nagae et al. | 600/437 |
| 2013/0255389 A1 | 10/2013 | Watanabe et al. | 73/655 |
| 2014/0010052 A1 | 1/2014 | Torashima et al. | 367/181 |
| 2015/0091477 A1 | 4/2015 | Kandori et al. | 318/116 |

FOREIGN PATENT DOCUMENTS

| | | |
|---|---|---|
| CN | 101883309 | 11/2011 |
| CN | 102458692 | 5/2012 |
| CN | 102596053 A | 7/2012 |
| EP | 0401027 | 12/1990 |
| EP | 2793048 A | 10/2014 |
| GB | 2114857 A | 8/1983 |
| JP | S58-161492 | 9/1983 |
| JP | H01-024479 | 5/1989 |
| JP | H01-024480 | 5/1989 |
| JP | H06-125894 | 5/1994 |
| JP | H07-193896 | 7/1995 |
| JP | 2004-350700 | 12/2004 |
| JP | 2004-350702 | 12/2004 |
| JP | 2004-350703 | 12/2004 |
| JP | 2005-103294 | 4/2005 |
| JP | 2005-117159 | 4/2005 |
| JP | 2008-098697 | 4/2008 |
| JP | 2010-183979 | 8/2010 |
| JP | 2012-217624 | 11/2012 |
| JP | 2012-234208 | 11/2012 |
| JP | 2014-017566 | 1/2014 |
| WO | WO 2010/073534 A | 7/2010 |
| WO | WO 2013/032021 A | 3/2013 |

OTHER PUBLICATIONS

Yaralioglu, Goksen G., et al. "Calculation and measurement of electromechanical coupling coefficient of capacitive micromachined ultrasonic transducers." Ultrasonics, Ferroelectrics, and Frequency Control, IEEE Transactions on 50.4 (2003): 449-456.*

Nikoozadeh, Amin, et al. "Analytical calculation of collapse voltage of CMUT membrane [capacitive micromachined ultrasonic transducers]." Ultrasonics Symposium, 2004 IEEE. vol. 1. IEEE, 2004.*

Ergun, Arif S., Goksen G. Yaralioglu, and Butrus T. Khuri-Yakub. "Capacitive micromachined ultrasonic transducers: Theory and technology." Journal of Aerospace Engineering 16.2 (2003): 76-84.*

Lohfink, Annette, and Peter-Christian Eccardt. "Linear and nonlinear equivalent circuit modeling of CMUTs." Ultrasonics, Ferroelectrics, and Frequency Control, IEEE Transactions on 52.12 (2005): 2163-2172.*

Wygant, Ira O., et al. "50 kHz capacitive micromachined ultrasonic transducers for generation of highly directional sound with parametric arrays." Ultrasonics, Ferroelectrics, and Frequency Control, IEEE Transactions on 56.1 (2009): 193-203.*

Nikoozadeh, Amin, and Pierre T. Khuri-Yakub. "CMUT with substrate-embedded springs for non-flexural plate movement." Ultrasonics Symposium (IUS), 2010 IEEE. IEEE, 2010.*

Wang, Mengli, et al. "Design and test of a monolithic ultrasound-image-guided HIFU device using annular CMUT rings." 2008 IEEE Ultrasonics Symposium. IEEE, 2008.*

Zahorian, Jaime S. "Fabrication technology and design for CMUTS on CMOS for IVUS catheters." (2013).*

Zhuang, Xuefeng. Capacitive micromachined ultrasonic transducers with through-wafer interconnects. ProQuest, 2008.*

Degertekin, F. Levent, Mustafa Karaman, and Rasim O. Guldiken. "Forward-looking IVUS imaging using an annular-ring CMUT array." IEEE Ultrasonics Symposium, 2005.. vol. 1. IEEE, 2005.*

Guldiken, Rasim, et al. "5G-5 Dual-Annular-Ring CMUT Array for ForwardLooking IVUS Imaging." 2006 IEEE Ultrasonics Symposium. IEEE, 2006.*

Savoia, A., Caliano, G., et al. "Multilayer cMUT Structure for Improved Sensitivity and Bandwidth." 2006 IEEE Ultrasonics Symposium. IEEE, 2006.*

JP 2014-17566 A. Jan. 30, 2014. English Machine Translation.*

H. Taki et al., "High Range Resolution Medical Acoustic Vascular Imaging with Frequency Domain Interferometry", *Proceedings of 32nd International Conference of the IEEE Engineering in Medicine and Biology Society*, pp. 5298-5301 ( 2010).

EESR issued on Jun. 2, 2015 in counterpart European patent application 14163664.7.

Extended European Search Report dated Aug. 14, 2015 in EPA 14163665.4 (in English).

H. Taki et al., "High Resolution Medical Acoustic Vascular Imaging Using Frequency Domain Interferometry", *Ninth IASTED International Conference on Visualization, Imaging and Image Processing (VIIP 2009)*, pp. 7-12 (Jul. 13, 2009).

Extended European Search Report dated May 12, 2015 in EPA 14163663.9 (in English).

Office Action dated Dec. 23, 2015 in counterpart P.R. China patent application 201410180728.7, with translation.

Office Action dated Jan. 13, 2016 in P.R. China patent application 201410171904.0, with translation.

Office Action dated Nov. 21, 2017 in Japanese patent application 2014-022479, with translation.

Office Action dated Nov. 21, 2017 in Japanese patent application 2014-022480, with translation.

Office Action dated Sep. 18, 2018, in corresponding CN Application No. 201710112853.8 (8 pages).

U.S. Appl. No. 14/251,735, filed Apr. 14, 2014.

* cited by examiner

CAPACITIVE TRANSDUCER AND METHOD OF MANUFACTURING SAME

BACKGROUND OF THE INVENTION

Field of the Invention

The present invention relates to a capacitive transducer and a method of manufacturing same.

Description of the Related Art

Conventionally, micromechanical components manufactured by micromachining technology have been processable in the order of micrometers. Through use thereof, various micro-functional elements have been realized. Capacitive transducers using such technology have been studied as a substitute for piezoelectric elements. With such a capacitive transducer, an ultrasound wave can be transmitted and received using vibration of a vibrating membrane, and excellent wideband characteristics particularly in liquid can be obtained easily.

There is a capacitive transducer including an element in which cells are arranged in a square shape or rectangle shape and the gaps between adjacent cells are uniform (see Japanese Patent Application Laid-open No. 2008-98697). Also, there is a capacitive transducer in which the transmission efficiency or receiving sensitivity of a cell in an end portion of an element is lower than the transmission efficiency or receiving sensitivity of a cell in a middle portion of the element (see U.S. Pat. No. 8,456,958).

Patent Literature 1: Japanese Patent Application Laid-open No. 2008-98697
Patent Literature 2: U.S. Pat. No. 8,456,958

SUMMARY OF THE INVENTION

In the case of transmitting an ultrasound wave with a capacitive transducer including an element in which cells are arranged in a square shape or rectangle shape and gaps between adjacent cells are uniform, the radiated sound pressure is uniform in an end portion and a middle portion of the element. Therefore, it is easy for a side lobe of an ultrasound beam to occur. The quality of an ultrasound image using the ultrasound beam may deteriorate due to the side lobe. The image quality may deteriorate in a similar manner in the case of reception as well.

In a capacitive transducer in which the transmission efficiency or receiving sensitivity of a cell in an end portion of an element is lower than in a middle portion, the structure is such that the shape of a cell in the end portion of the element and the shape of a cell in the middle portion differ. With this configuration, apodization by which a side lobe is reduced is possible. However, since the frequency characteristics of the transmission efficiency and the receiving sensitivity differ for each cell, the S/N ratio may deteriorate due to a signal in an unnecessary frequency band being acquired particularly at the time of receiving an ultrasound wave.

The present invention has been made based on recognition of such a task. An object of the present invention is to reduce a side lobe in a capacitive transducer.

The present invention provides a capacitive transducer comprising:
an element including a plurality of cells supported such that a vibrating membrane including one of a pair of electrodes formed with an gap inbetween is capable of vibration, wherein
a distance between a pair of electrodes of a cell in an end portion of the element is greater than a distance between a pair of electrodes of a cell in a middle portion of the element.

The present invention also provides a method of manufacturing a capacitive transducer including an element including a plurality of cells,
the method comprising the steps of:
forming a plurality of first electrodes; and
forming a vibrating membrane capable of vibration and including a plurality of second electrodes paired with the plurality of first electrodes respectively to thereby form a plurality of the cells including a pair of the first electrode and the second electrode, wherein
a distance between the first electrode and the second electrode in a cell in an end portion of the element is greater than a distance between the first electrode and the second electrode in a cell in a middle portion of the element in the step of formation.

With the present invention, a side lobe in a capacitive transducer can be reduced.

Further features of the present invention will become apparent from the following description of exemplary embodiments with reference to the attached drawings.

DESCRIPTION OF THE EMBODIMENTS

Figure 1A:
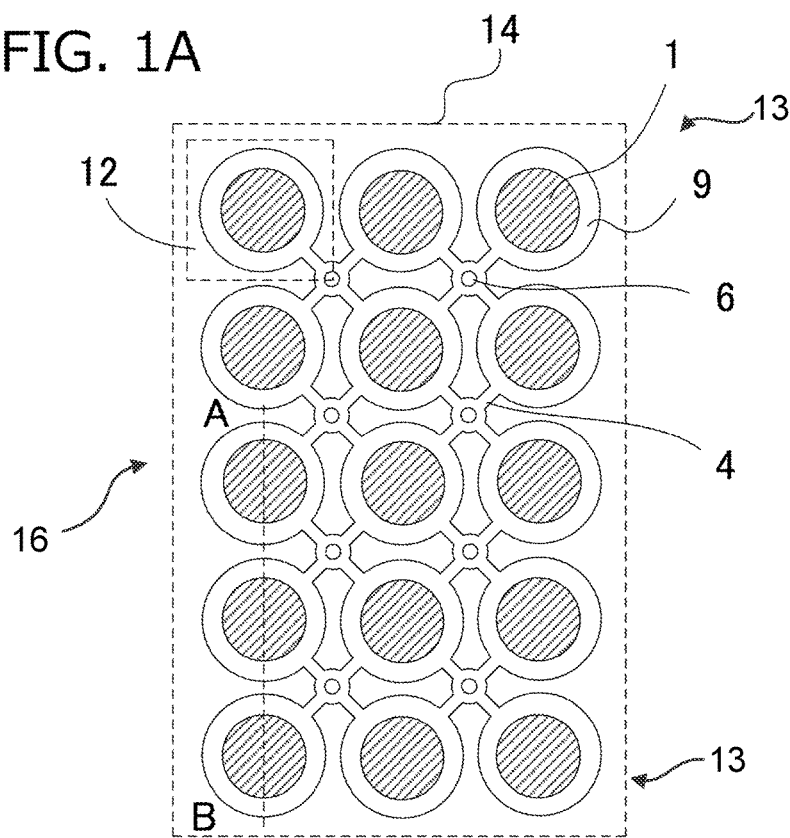
FIGS. 1A and 1B are a top view and a sectional view along line A-B of a capacitive transducer in Example 1.

A preferred embodiment of the present invention will be described below with reference to the drawings. Note that the dimension, material, and shape of components, the relative arrangement thereof, and the like described below should be changed appropriately depending on the configuration of an apparatus or various conditions to which the invention is applied and are not intended to limit the scope of the invention to the description below.

The present invention has been made for a capacitive transducer for an ultrasound wave and can be applied to an apparatus and a method for transmitting or receiving an ultrasound wave using the transducer. Further, the subject matter of the present invention includes an apparatus utilizing an ultrasound echo technique in which an ultrasound wave is transmitted to an object such as a living body and an echo wave reflected and propagated inside the object is received. By data generation based on the echo wave, characteristic information reflecting the difference in acoustic impedance inside the object can be acquired.

The capacitive transducer of the present invention can be utilized in receiving, besides an echo wave, a photoacoustic wave generated and propagated by a light absorber inside an object through a photoacoustic effect when the object is irradiated with light from a light source. By analyzing the photoacoustic wave, functional information or optical characteristic information relating to the inside of the object can be acquired. Such apparatuses obtain characteristic information by performing analysis with an information processing device after processing by a signal processing unit has been performed with respect to a received echo wave or photoacoustic wave, and therefore can be referred to as object information acquiring apparatus. By displaying the characteristic information as image data in a display unit, internal examination such as a diagnosis is possible.

The present invention can also be understood as a method of controlling an object information acquiring apparatus, an object information acquiring method, or an acoustic wave measurement method. Further, the present invention can also be understood as a program that realizes such a method with an information processing unit such as a CPU or circuit. The present invention can also be understood as a method of manufacturing a capacitive transducer characteristic to the present invention or a method of manufacturing a probe using the same.

In the case of using a capacitive transducer for acquiring characteristic information, use of a probe in which a single or a plurality of elements are arranged is preferable. By holding an object for scanning with the probe, measurement over a wide range is possible. If the object is a breast, it is preferable to use, for example, a plate-shaped member or cup-shaped member for holding.

An ultrasound wave referred to in the present invention is given as a typical example of an acoustic wave also called a sound wave or elastic wave. The wavelength or the like is not limited.

Figure 1B:
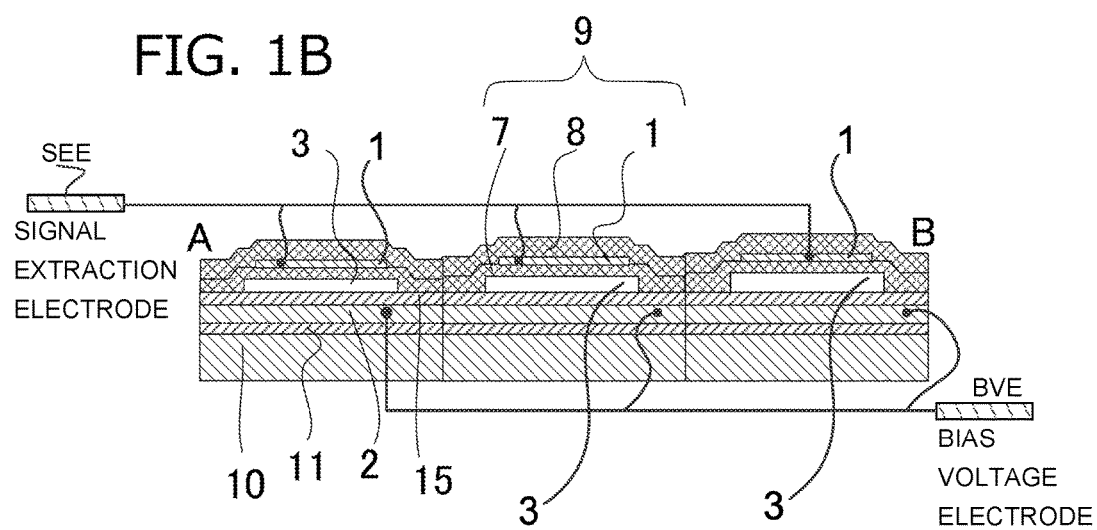

An embodiment of the present invention will be described below using FIGS. 1A and 1B. FIG. 1A is a top view of a capacitive transducer of the present invention, and FIG. 1B is a sectional view along line A-B in FIG. 1A. In an element 14 of the capacitive transducer of the present invention, a plurality of cells 12 are formed (for the sake of clarity in the drawing, only one cell is actually given a reference character in FIG. 1A). The number of elements 14 included in the capacitive transducer is one in FIG. 1A, but may be any number. Herein, "element" refers to each element 14 of the capacitive transducer of which a signal extraction electrode SEE is shared by all cells 12 forming the element. That is, output of an electrical signal is performed in terms of these elements. The number of cells 12 included in the element 14 is fifteen in FIG. 1A, but may be any number.

In each cell 12, a vibrating membrane 9 is supported to be capable of vibration. The vibrating membrane 9 includes a second electrode 1. The second electrode 1 is provided such that a first electrode 2 is across a gap 3 (i.e., cavity). In FIG. 1B, the vibrating membrane has a configuration in which the second electrode 1 is sandwiched between a first membrane 7 and a second membrane 8. However, a configuration with only the second electrode or only the first membrane and the second electrode is acceptable, as long as the vibrating membrane is capable of vibration and includes the second electrode. As will be described later, reference numeral 4 denotes an etching path, reference numeral 6 denotes a sealing portion, reference numeral 10 denotes a substrate, and reference numerals 11 and 15 denote first and second insulating films.

The first electrode or the second electrode is used as an electrode for applying bias voltage or an electrode for adding an electrical signal or extracting an electrical signal. Although the first electrode is used as an electrode for applying bias voltage and the second electrode is used as a signal extraction electrode in FIGS. 1A and 1B, it may be the opposite. The electrode BVE for applying bias voltage is also shared within an element. The configuration may be such that the bias voltage is shared between elements. However, the signal extraction electrode has to be electrically separated for each element.

In the element of the capacitive transducer in FIGS. 1A and 1B, the gap between a pair of electrodes of a cell 12 in an end portion 13 of the element 14 is greater than the gap between a pair of electrodes of a cell 12 in a middle portion 16 of the element 14 (compare the smaller gap in the cell at the left of FIG. 1B with the larger gap in the cell at the right of that FIG.). Since the transmission efficiency or receiving sensitivity is lower when the gap between a pair of electrodes of a cell is greater, the transmission efficiency or receiving sensitivity of a cell in the end portion 13 of the element 14 can be made low. Thus, compared to a capacitive transducer having the same transmission efficiency or receiving sensitivity throughout an element from a middle portion to an end portion, a side lobe that occurs on the side of an ultrasound beam can be reduced. Therefore, an ultrasound signal not along the direction of an ultrasound beam and from a target can be reduced, and a high-quality ultrasound image can be formed.

Further, the spring constant of a vibrating membrane of a cell 12 in the end portion 13 of the element 14 can be made smaller than the spring constant of a vibrating membrane of a cell 12 in the middle portion 16 of the element 14. The frequency characteristics of the transmission efficiency or receiving sensitivity are determined by the effective spring constant of a cell 12. The effective spring constant depends on the force of the electrostatic force (between the charged electrodes) subtracted from the restoring force of a spring of a vibrating membrane. In the capacitive transducer of this configuration, the gap between a pair of electrodes of a cell 12 in the end portion 13 of the element 14 is greater than the gap between a pair of electrodes of a cell 12 in the middle portion 16 of the element 14. Therefore, the electrostatic force of a cell 12 in the end portion 13 of the element 14 is smaller than the electrostatic force of a cell 12 in the middle portion 16 of the element 14.

By causing the spring constant of a vibrating membrane of a cell 12 in the end portion 13 of the element 14 to be smaller than the spring constant of a vibrating membrane of a cell 12 in the middle portion 16 of the element 14 as in this configuration, the effective spring constant of all cells within the element 14 can be made the same. Accordingly, the frequency characteristics of the transmission efficiency and the receiving sensitivity of all cells forming the element become approximately the same. Thus, since a signal in an unnecessary frequency band is not acquired at the time of receiving an ultrasound wave, the S/N ratio does not deteriorate, and deterioration in image quality can be prevented. Therefore, since apodization by which a side lobe is reduced is possible and deterioration in S/N ratio can be reduced with the capacitive transducer of this configuration, a high-quality ultrasound image can be formed.

Further, the configuration may be such that the sum of the restoring force and the electrostatic force of a vibrating membrane of a cell 12 in the end portion of the element and the sum of the restoring force and the electrostatic force of a vibrating membrane of a cell 12 in the middle portion of the element are equal. With the capacitive transducer of this configuration, the effective spring constant of all cells 12 within the element can be made the same, and the frequency characteristics of the transmission efficiency and the receiving sensitivity of all cells 12 forming the element become the same. Thus, since a signal in an unnecessary frequency band is not acquired at the time of receiving an ultrasound wave, the S/N ratio does not deteriorate, and deterioration in image quality can be prevented. Therefore, since apodization by which a side lobe is reduced is possible and deterioration in S/N ratio can be reduced with the capacitive transducer of this configuration, a high-quality ultrasound image can be formed.

For example, in the case where the shape of a vibrating membrane is a circle, a restoring force $F_M$ can be described with formula (1):

$$F_M = k_M \cdot x \qquad (1)$$

Herein, $K_M$ is the spring constant of a vibrating membrane, and x is the displacement amount of the vibrating membrane.

An electrostatic force $F_E$ can be described with formula (2):

[Math. 1]

$$F_E = \frac{1}{2} \frac{\varepsilon_0 S}{d-x} V^2 \qquad (2)$$

Herein, $\varepsilon_0$ is the dielectric constant of vacuum, S is the area of the vibrating membrane, V is the bias voltage, and d is the effective distance before the bias voltage is applied.

The sum of the restoring force and the electrostatic force of a vibrating membrane of a cell can be described with formula (3):

[Math. 2]

$$F = k_M \cdot x - \frac{1}{2} \frac{\varepsilon_0 S}{d-x} V^2 \qquad (3)$$

Therefore, the effective spring constant of a cell can be described with formula (4):

[Math. 3]

$$k = k_M - \frac{1}{2} \frac{\varepsilon_0 S}{(d-x)^2} V^2 \qquad (4)$$

The sum of the restoring force and the electrostatic force of a vibrating membrane of a cell 12 in the end portion of the element and the sum of the restoring force and the electrostatic force of a vibrating membrane of a cell 12 in the middle portion of the element are "equal," i.e., may be exactly the same or may be equal in terms of the respective effective spring constants. The effective spring constants of cells 12 in the middle portion and the end portion of an element can be described with formula (5) in which c and e are respectively added as subscripts:

[Math. 4]

$$kc = ke \qquad (5)$$
$$k_{Mc} - k_{Me} = \frac{1}{2}\left(\frac{S_c}{(d_c-x)^2} - \frac{S_e}{(d_e-x)^2}\right)V^2$$

Since $d_e > d_c$ herein, $k_{Me} < k_{Mc}$. By determining the spring constant in the end portion and the spring constant in the middle portion of the element to satisfy formula (5), the frequency characteristics of the transmission efficiency and the receiving sensitivity of all cells 12 forming the element can be made the same. Thus, since a signal in an unnecessary frequency band is not acquired at the time of receiving an ultrasound wave, the S/N ratio does not deteriorate, and deterioration in image quality can be prevented. Therefore, since apodization by which a side lobe is reduced is possible and deterioration in S/N ratio can be reduced with the capacitive transducer of this configuration, a high-quality ultrasound image can be formed.

The driving principle of the present invention will be described. By using a signal extraction wire, the capacitive transducer can extract an electrical signal from the second electrode. An electrical signal is extracted by an extraction wire in this embodiment, but a through wire or the like may be used. An electrical signal is extracted from the second electrode in this embodiment, but may be extracted from the first electrode.

In the case of receiving an ultrasound wave with the capacitive transducer, a DC voltage is applied to the first electrode 2 by voltage applying means (not shown) to generate a difference in potential between electrodes. In this case, it is recommended that the second electrode 1 be fixed at ground voltage. The ground voltage shows a reference potential in direct current of a current-voltage conversion circuit (receiving circuit) (not shown). When an ultrasound wave is incident, the vibrating membrane 9 including the second electrode 1 is deformed. Therefore, the distance of the gap 3 between the second electrode 1 and the first electrode 2 changes, thereby changing the capacitance. Due to the change in capacitance, current is output from the second electrode 1, and current flows in an extraction wire. The current is converted into voltage by a current-voltage conversion circuit (not shown), and the ultrasound wave can be received. As described above, the configuration of an extraction wire may be changed such that a DC voltage is applied to the second electrode, and an electrical signal is extracted from the first electrode. The current-voltage conversion circuit is preferably provided within a probe 402 in FIG. 4.

In the case of transmitting an ultrasound wave, an AC voltage (including pulse voltage) is applied as a transmission signal to the second electrode 1 in a state where a difference in potential is generated between the first electrode 2 and the second electrode 1, so that the vibrating membrane 9 can be vibrated by the electrostatic force. Accordingly, an ultrasound wave can be transmitted. The configuration of an extraction wire may be changed in the case of transmission as well, such that an AC voltage is applied to the first electrode to vibrate a vibrating membrane.

Using FIGS. 3A to 3F, a preparation method of the present invention will be described. FIGS. 3A to 3F are sectional views of a capacitive transducer of the present invention of which the configuration is approximately similar to FIG. 1B. FIGS. 3A to 3F are sectional views along line A-B in FIG. 1A.

Figure 3A:
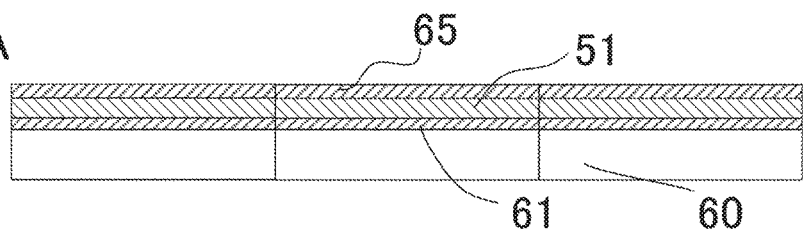
FIGS. 3A to 3F are sectional views along line A-B illustrating a method of preparing a capacitive transducer.

As shown in FIG. 3A, a first insulating film 61 is formed on a substrate 60. The substrate 60 is a silicon substrate, and the first insulating film 61 is provided for insulation from a first electrode. In the case where the substrate 60 is an insulating substrate such as a glass substrate, the first insulating film 61 may be omitted. The substrate 60 is preferably a substrate with a small surface roughness. In the case where the surface roughness is large, the surface roughness is transferred in a membrane forming step that is a step after this step, causing variation among respective cells and respective elements in the distance between the first electrode and a second electrode due to the surface roughness. The variation results in variation in the sensitivity of transmission and reception. Therefore, the substrate 60 is preferably a substrate with a small surface roughness.

Next, a first electrode 51 is formed. For the first electrode 51, a conductive material with a small surface roughness, e.g., titanium or aluminum, is preferable. In the case where the surface roughness of the first electrode is large, variation is caused among respective cells and respective elements in the distance between the first electrode and the second electrode due to the surface roughness in a similar manner to the substrate. Therefore, a conductive material with a small surface roughness is preferable.

Next, a second insulating film 65 is formed. The second insulating film 65 is formed preferably of an insulating material with a small surface roughness in order to prevent an electrical short circuit or dielectric breakdown between the first electrode and the second electrode in the case where voltage is applied between the first electrode and the second electrode. In the case of driving with low voltage, the second insulating film 65 may be omitted, since a first membrane layer (described below) is an insulator. In the case where the surface roughness of the second insulating film is large, variation is caused among respective cells and respective elements in the distance between the first electrode and the second electrode due to the surface roughness in a similar manner to the substrate. Therefore, a second insulating film with a small surface roughness is preferable. Examples include a silicon nitride film and a silicon oxide film.

Figure 3B:
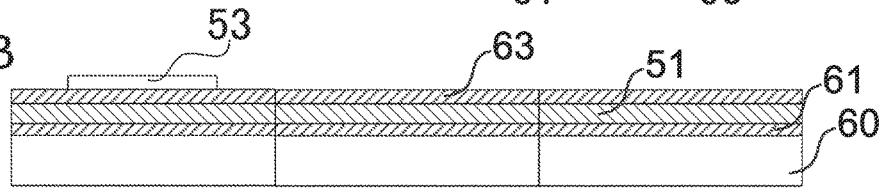

Next, as shown in FIG. 3B, a sacrificial layer 53 is formed (for the sake of clarity in the drawings, the sacrificial layers are not cross-hatched). For the sacrificial layer 53, a material with a small surface roughness is preferable. In the case where the surface roughness of the sacrificial layer is large, variation is caused among respective cells and respective elements in the distance between the first electrode and the second electrode due to the surface roughness in a similar manner to the substrate. Therefore, a sacrificial layer with a small surface roughness is preferable. In order to shorten the time for etching in which the sacrificial layer is removed, a material with which the etching speed is fast is preferable.

The material of a sacrificial layer is desired to be such that the second insulating film, the first membrane layer, and the second electrode are almost not etched by etching liquid or etching gas for removing the sacrificial layer. In the case where the second insulating film, the first membrane layer, and the second electrode are nearly etched by etching liquid or etching gas for removing a sacrificial layer, variation in the thickness of a vibrating membrane and variation in the distance between the first electrode and the second electrode occur. The variation in thickness of the vibrating membrane and the variation in the distance between the first electrode and the second electrode become variation in sensitivity among respective cells and among respective elements. In the case where the second insulating film and the first membrane layer are a silicon nitride film or silicon oxide film, chromium with a small surface roughness and for which an etching liquid does not cause etching of the second insulating film, the first membrane layer, and the second electrode is preferable.

Figure 3C:
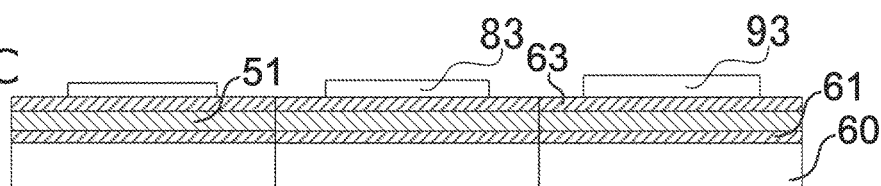

Next, as shown in FIG. 3C, a sacrificial layer 83 and a sacrificial layer 93 are formed by repeating the step in FIG. 3B. The sacrificial layer 53 is for forming a gap in a cell in a middle portion of an element, and the sacrificial layer 83 and the sacrificial layer 93 are for forming a gap in a cell toward an end portion of the element. Therefore, the sacrificial layer 53 is thinner than the sacrificial layer 83, and the sacrificial layer 83 is thinner than the sacrificial layer 93.

With FIG. 3D to FIG. 3F, steps of forming the vibrating membrane including the second electrode and forming a gap through removal of a sacrificial layer will be described. The vibrating membrane is formed of a first membrane, the second electrode, and a second membrane in FIGS. 3A to 3F, but may be formed with any number of layers as long as the second electrode is included.

Figure 3D:
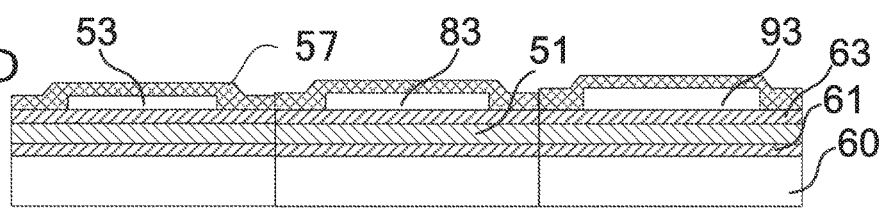

As shown in FIG. 3D, a first membrane layer 57 including the first membrane is formed. For the first membrane layer 57, low tensile stress is preferable. For example, tensile stress of 300 MPa or less is preferable. With a silicon nitride film, control of stress is possible, and the tensile stress can be made 300 MPa or less. In the case where the first membrane has compressive stress, the first membrane becomes highly deformed due to sticking or buckling. In the case of large tensile stress, the first membrane may be broken. Therefore, for the first membrane layer 57, low tensile stress is preferable.

Figure 3E:
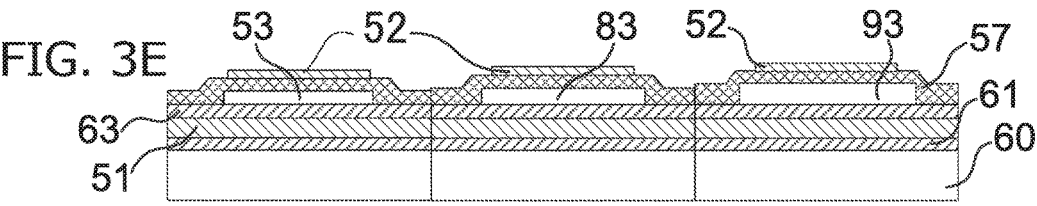

Next, as shown in FIG. 3E, a second electrode 52 is formed, and an etching hole (not shown) is further formed. Then, the sacrificial layer 53, the sacrificial layer 83, and the sacrificial layer 93 are removed through the etching hole via an etching path (not shown). For the second electrode 52, a material with small residual stress and having heat resistance is preferable. In the case where residual stress of the second electrode is large, the vibrating membrane becomes highly deformed. Therefore, a second electrode with small residual stress is preferable. It is preferable that a material not cause transformation or an increase in stress depending on the temperature or the like upon forming a second membrane layer or a sealing layer for forming a sealing portion.

In the case of performing removal of a sacrificial layer in a state where the second electrode is exposed, etching of a sacrificial layer needs to be performed while a photoresist or the like for protection of the second electrode is applied. Since stress due to the photoresist or the like facilitates sticking of the first membrane, it is preferable that the second electrode have etching resistance such that etching of a sacrificial layer is feasible in a state where the second electrode is exposed without a photoresist. Sticking refers to the adhesion of the vibrating membrane as a structure after removal of a sacrificial layer. For example, titanium, aluminum-silicon alloy or the like is preferable.

Figure 3F:
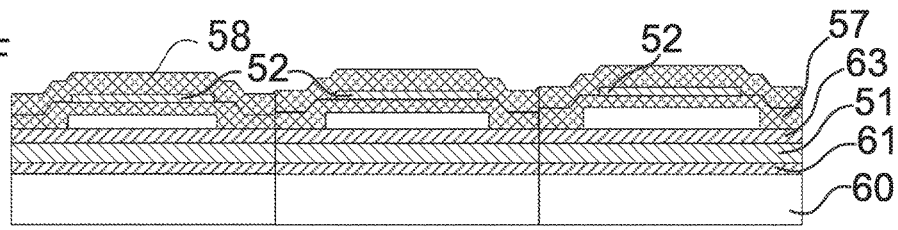

Next, as shown in FIG. 3F, a second membrane layer 58 including the second membrane is formed. In this step, the second membrane is formed, and the sealing portion for sealing the etching hole (not shown) is formed. By forming the second membrane layer 58, the second membrane is formed to form the vibrating membrane having a desired spring constant and enable sealing of the etching hole.

In the case where a step of sealing the etching hole and a step of forming the second membrane are the same as in this step, the vibrating membrane can be formed with only the membrane forming step. Therefore, since it is easy to control the thickness of the vibrating membrane and variation in the spring constant or variation in the deflection of the vibrating membrane due to variation in the thickness can be reduced, variation in the receiving or transmitting sensitivity among cells or elements can be reduced.

The step of sealing the etching hole and the step of forming the second membrane may be separate steps. It may be such that the sealing portion is formed after the second membrane is formed, or the second membrane is formed after the sealing portion is formed.

For the second membrane layer, a material having low tensile stress is preferable. In the case where the second membrane has compressive stress in a similar manner to the first membrane, the first membrane becomes highly deformed due to sticking or buckling. In the case of large tensile stress, the second membrane may be broken. Therefore, for the second membrane layer, low tensile stress is preferable. With a silicon nitride film, control of stress is possible, and the tensile stress can be made 300 MPa or less.

For the sealing portion, it suffices that liquid or external air be prevented from entering into the gap. Particularly, in the case of sealing under reduced pressure, the vibrating membrane is deformed by atmospheric pressure, and the distance between the first electrode and the second electrode decreases. Since the transmitting or receiving sensitivity is proportional to the effective distance between the first electrode and the second electrode raised to the power of 1.5, the transmitting or receiving sensitivity can be improved through sealing under reduced pressure such that the pressure in the gap is lower than the atmospheric pressure. The effective distance takes into consideration the gap and a value for the insulating film for the first electrode and the second electrode obtained through division by the dielectric constant.

After this step, a wire connecting the first electrode and the second electrode is formed by a step that is not shown. The material for the wire may be aluminum or the like.

With such a manufacturing method, a capacitive transducer having a configuration necessary for achieving the object of the present invention can be manufactured.

A more specific example will be given below for a detailed description of the present invention.

Example 1

An embodiment of the present invention will be described below using FIGS. 1A and 1B. FIG. 1A is a top view of the capacitive transducer of the present invention, and FIG. 1B is a sectional view along line A-B in FIG. 1A. The element 14 of the capacitive transducer of the present invention is formed of fifteen cells 12. The number of elements 14 included in the capacitive transducer is one in FIG. 1A, but may be any number.

The cell 12 is supported such that the vibrating membrane 9 including the second electrode 1 provided across the gap 3 from the first electrode 2 is capable of vibration. The vibrating membrane 9 has a configuration in which the second electrode 1 is sandwiched between the first membrane 7 and the second membrane 8. The first electrode 2 is an electrode for applying bias voltage, and the second electrode 1 is a signal extraction electrode. The shape of the vibrating membrane in this example is a circle. However, the shape may be a quadrangle, hexagon, or the like. In the case of a circle, the vibrational mode is axisymmetric. Therefore, vibration of the vibrating membrane due to an unnecessary vibrational mode can be reduced.

The first insulating film 11 on the silicon substrate 10 is a silicon oxide film formed by thermal oxidation and with a thickness of 1 µm. The second insulating film 15 is a silicon oxide film formed by plasma-enhanced chemical vapor deposition (PE-CVD) and with a thickness of 0.1 µm. The first electrode is aluminum with a thickness of 50 nm, and the second electrode 1 is aluminum with a thickness of 100 nm. The first membrane 7 and the second membrane 8 are silicon nitride films prepared by PE-CVD and are formed with tensile stress of 200 MPa or less. The diameter of the first membrane 7 and the second membrane 8 is 25 µm. The respective thicknesses are 0.4 µm and 0.7 µm.

In the element of the capacitive transducer in FIGS. 1A and 1B, the gap between a pair of electrodes of a cell in the end portion of the element is greater than the gap between a pair of electrodes of a cell in the middle portion of the element. The depth of a gap in a cell in the end portion of the element is 0.25 µm, and the respective depths of the gap are 0.2 µm and 0.15 µm for cells toward the middle portion of the element. Since the transmission efficiency or receiving sensitivity is lower when the gap between a pair of electrodes of a cell is greater, the transmission efficiency or receiving sensitivity of a cell in the end portion of the element can be made low with this configuration. Thus, compared to a capacitive transducer having the same transmission efficiency or receiving sensitivity throughout an element from a middle portion to an end portion, a side lobe that occurs on the side of an ultrasound beam can be reduced. Therefore, an ultrasound signal not along the direction of an ultrasound beam and from a target can be reduced, and a high-quality ultrasound image can be formed.

It suffices that the gap between a pair of electrodes of a cell 12 in the end portion of the element be greater than the gap between a pair of electrodes of a cell in the middle portion of the element, and it suffices that the depth of a gap, the thickness of a first insulating film, and the thickness of a vibrating membrane of a cell in the end portion of the element be greater than the depth of a gap, the thickness of a first insulating film, and the thickness of a vibrating membrane of a cell in the middle portion of the element. In the case where the thickness of a vibrating membrane of a cell in the end portion of the element is greater than the thickness of a vibrating membrane of a cell in the middle portion of the element, the size of a vibrating membrane of a cell in the end portion of the element is made greater than the size of a vibrating membrane of a cell in the middle portion of the element. Accordingly, the spring constant of a vibrating membrane of a cell in the end portion of the element can be made the same as the spring constant of a vibrating membrane of a cell in the middle portion of the element, and the frequency characteristics of the transmission efficiency or receiving sensitivity of all cells within the element can be made the same.

The depth of a gap and the thickness of a first insulating film of a cell in the end portion of the element are preferably greater than the depth of a gap and the thickness of a first insulating film of a cell in the middle portion of the element. With this configuration, the size of a vibrating membrane of all cells within the element can be made the same, and therefore design is easy. The radiation impedance of all cells within the element can be made the same, and etching time for a sacrificial layer for all cells within the element can be made the same.

It suffices that the gap between a pair of electrodes of a cell in the end portion of the element and the gap between a pair of cells in the middle portion of the element be designed depending on the shape of an intended ultrasound beam. For example, the design may be in accordance with the distribution of a Gaussian beam.

Since the shape of a vibrating membrane of a cell is the same within the element, the frequency characteristics of the transmission efficiency and the receiving sensitivity of all cells forming the element are approximately the same. Thus, since a signal in an unnecessary frequency band is not acquired at the time of receiving an ultrasound wave, the SN ratio does not deteriorate, and deterioration in image quality can be prevented. Therefore, since apodization by which a side lobe is reduced is possible and deterioration in the S/N ratio can be reduced with the capacitive transducer of this configuration, a high-quality ultrasound image can be formed. The shape of a cell is "the same," i.e., the shape may be exactly the same or may include an error, such as an error due to a manufacturing process, to a degree that the frequency characteristics of the conversion efficiency of a cell can be regarded the same.

Example 2

Figure 2A:
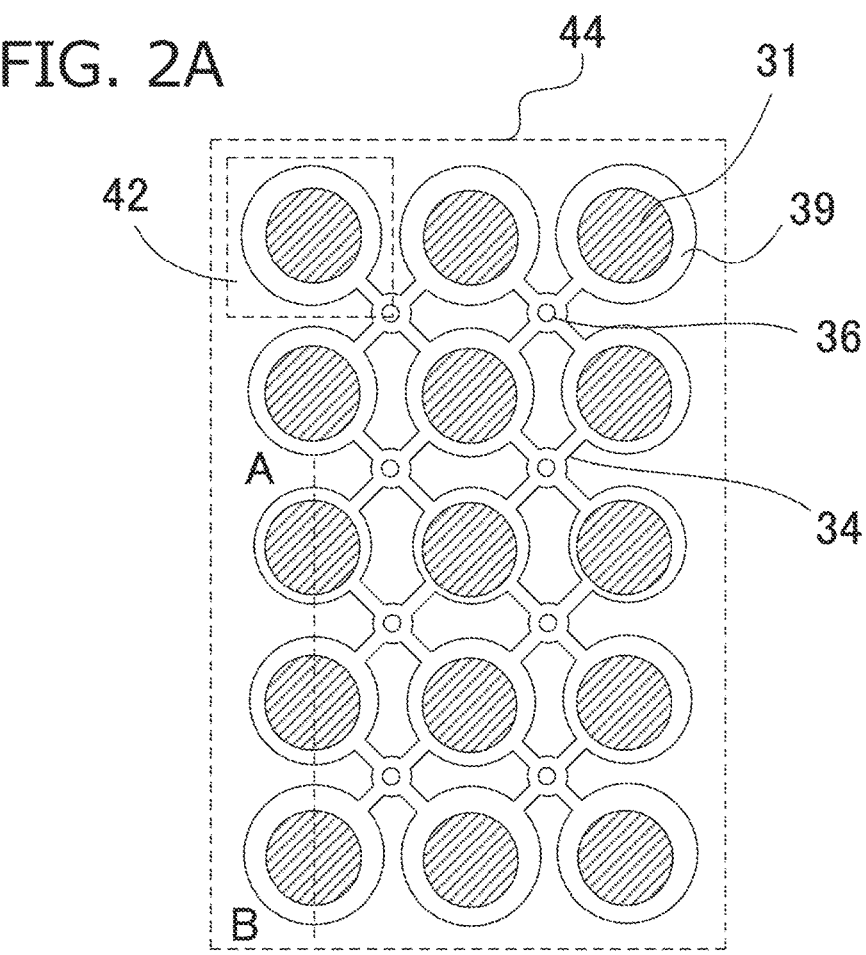
FIGS. 2A and 2B are a top view and a sectional view along line A-B of a capacitive transducer in Example 2.

The configuration of a capacitive transducer of Example 2 will be described using FIGS. 2A and 2B. FIG. 2A is a top view of the capacitive transducer of the present invention. Example 2 is approximately similar to Example 1 in the configuration of the capacitive transducer. Thus, the differences will be mainly described.

Figure 2B:
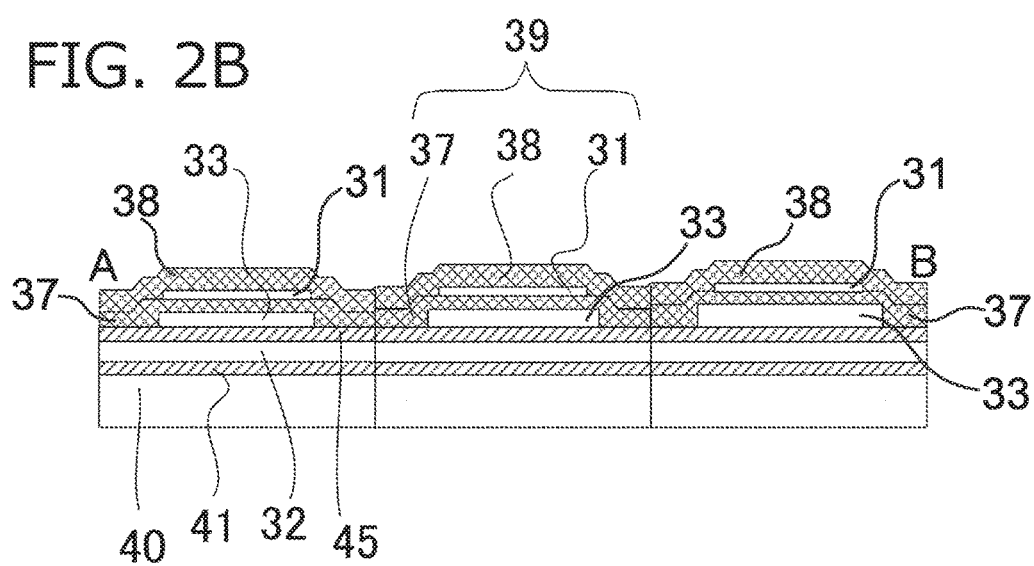

The capacitive transducer in FIGS. 2A and 2B includes a second electrode 31, a first electrode 32, a gap 33, an etching path 34, a sealing portion 36, a first membrane 37, a second membrane 38, a vibrating membrane 39, a substrate 40, a first insulating film 41, a cell 42, an element 44, and a second insulating film 45.

In the element of the capacitive transducer in FIGS. 2A and 2B, the spring constant of a vibrating membrane of a cell in an end portion of the element is smaller than the spring constant of a vibrating membrane of a cell in a middle portion of the element. The frequency characteristics of the transmission efficiency or receiving sensitivity are determined by the effective spring constant of a cell. The effective spring constant depends on the force of the electrostatic force subtracted from the restoring force of a spring of a vibrating membrane. Since the gap between a pair of electrodes of a cell in the end portion of the element is greater than the gap between a pair of electrodes of a cell in the middle portion of the element in the capacitive transducer of this configuration, the electrostatic force of a cell in the end portion of the element is smaller than the electrostatic force of a cell in the middle portion of the element.

With a configuration in which the spring constant of a vibrating membrane of a cell in the end portion of the element is smaller than the spring constant of a vibrating membrane of a cell in the middle portion of the element as in this configuration, the effective spring constant of all cells within the element can be made the same. Thus, the frequency characteristics of the transmission efficiency and the receiving sensitivity of all cells forming the element become approximately the same. Thus, since a signal in an unnecessary frequency band is not acquired at the time of receiving an ultrasound wave, the S/N ratio does not deteriorate, and deterioration in image quality can be prevented. Therefore, since apodization by which a side lobe is reduced is possible and deterioration in S/N ratio can be reduced with the capacitive transducer of this configuration, a high-quality ultrasound image can be formed.

In the capacitive transducer according to the present invention, as described above, the gap between a pair of electrodes of a cell in the end portion of the element is greater than the gap between a pair of electrodes of a cell in the middle portion of the element. Since the transmission efficiency or receiving sensitivity is lower when the gap between a pair of electrodes of a cell is greater, the transmission efficiency or receiving sensitivity of a cell in the end portion of the element can be made lower than the transmission efficiency or receiving sensitivity of a cell in the middle portion of the element. Thus, compared to a capacitive transducer having the same transmission efficiency or receiving sensitivity throughout an element from a middle portion to an end portion, a side lobe that occurs on the side of an ultrasound beam can be reduced. Therefore, an ultrasound signal not along the direction of an ultrasound beam and from a target can be reduced, and a high-quality ultrasound image can be formed.

Application Example

The capacitive transducer described above can be applied to a probe that receives or transmits an acoustic wave using the same. For example, in FIG. 4, the probe 402 includes a plurality of elements 403. By a transmission unit 405 performing control of a transmitted acoustic wave according to a command by an information processing unit 406, an acoustic wave is generated from each element. At the time of reception, an electrical signal output from each element is subjected to processing (e.g., amplification or AD conversion) by a signal processing unit 404.

Figure 4:
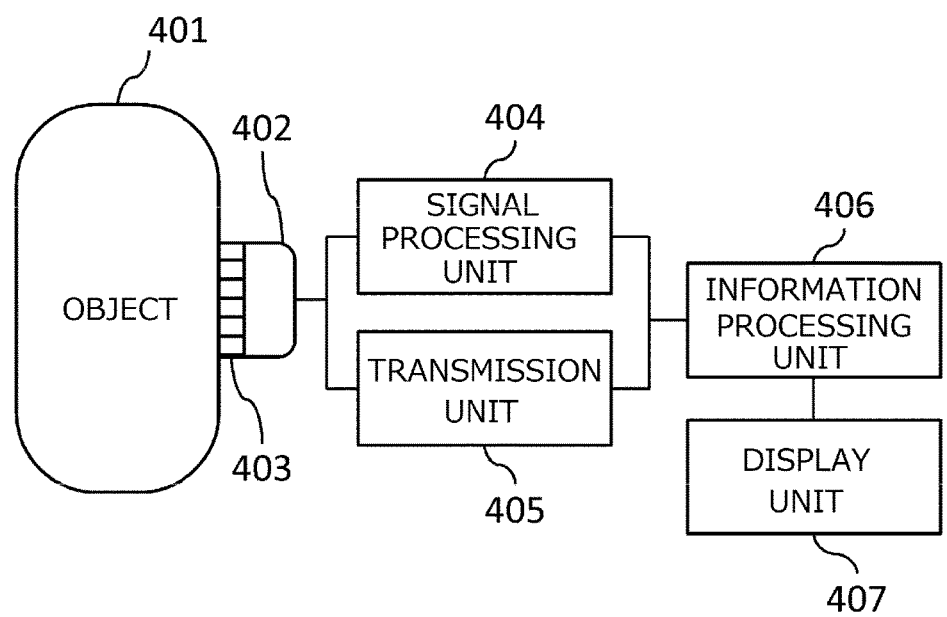
FIG. 4 is a block diagram illustrating the configuration of an object information acquiring apparatus.

FIG. 4 shows the probe described above being used as a component of an object information acquiring apparatus.

First, a case where a light absorber inside an object 401 absorbs light from a light source (not shown) to generate a photoacoustic wave as characteristic information will be described. At this time, the photoacoustic wave propagates inside the object and is received by the element. An electrical signal output from the element is input to the signal processing unit and subjected to signal processing. Based on a signal input from the signal processing unit, the information processing unit generates initial sound pressure distribution, absorption coefficient distribution, or the like of the inside of the object by known image reconstruction processing. Upon diagnosis, such information may be displayed in a display unit 407 as image data according to necessity. In this specification, a configuration formed of the signal processing unit and the information processing unit may be referred to as processing unit.

Next, a case of acquiring echo information relating to the inside of an object will be described. With a control signal sent by the transmission unit at this time, an acoustic wave is transmitted from each element. The acoustic wave reflected at the acoustic impedance boundary inside the object is received again by the element. A receive signal output from the element is subjected to known signal processing, reconstruction processing, or image data generation, in a similar manner to the case of a photoacoustic wave. In the case of an apparatus using the reflected wave, a probe for transmission of an acoustic wave may be provided separately from a probe for reception.

Further, the capacitive transducer of the present invention can be applied to an apparatus having both functions as an apparatus using a photoacoustic wave and an apparatus using an echo wave.

The probe may be for mechanical scanning or may be a probe (of a handheld type) that is grasped by a user such as a doctor or technician and moved with respect to an object. Particularly in the case of mechanically scanning an object that is a living body, stable measurement is made possible by holding the object with holding means. If the object is a breast, a plate-shaped or cup-shaped holding means is suitable.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-092668, filed on Apr. 25, 2013, and Japanese Patent Application No. 2014-022479, filed on Feb. 7, 2014, which are hereby incorporated by reference herein in their entirety.

What is claimed is:

1. A capacitive transducer comprising:
    an element including a plurality of cells, the element having an end portion and a middle portion, and having at least one of the cells in the end portion and at least one of the cells in the middle portion;
    wherein each cell has a first electrode and a second electrode which is included by a vibrating membrane,
    wherein the first electrode and the second electrode are formed separated by a distance, and
    wherein a shape of the element is rectangular having a pair of long sides and a pair of short sides, and, in a direction along a long side, the distance between the first electrode and the second electrode in the at least one cell in the end portion is greater than the distance between the first electrode and the second electrode in the at least one cell in the middle portion of the element.

2. The capacitive transducer according to claim 1, wherein the vibrating membrane of the at least one cell in the end portion has a spring constant that is smaller than the spring constant of the vibrating membrane of the at least one cell in the middle portion.

3. The capacitive transducer according to claim 1, wherein, in the element, the at least one cell in the end portion and the at least one cell in the middle portion are structured such that in each cell charges on the electrodes impose an electrostatic force $F_E$ on the vibrating membrane of that cell, and the at least one cell in the end portion and the at least one cell in the middle portion are further structured such that a restoring force $F_{Me}$ of the vibrating membrane of the at least one cell in the end portion is less than a restoring force $F_{Mm}$ of the vibrating membrane of the at least one cell in the middle portion by such an amount that a sum $F_{Me}+F_{Ee}$ of the restoring force and the electrostatic force on the vibrating membrane of the at least one cell in the end portion is equal to the sum $F_{Mm}+F_{Em}$ of the restoring force and the electrostatic force on the vibrating membrane of the at least one cell in the middle portion, where $F_{Ee}$ is the electrostatic force of the at least one cell in the end portion and $F_{Em}$ is the electrostatic force of the at least one cell in the end portion.

4. A probe comprising the capacitive transducer according to claim 1.

5. An object information acquiring apparatus comprising:
    the capacitive transducer according to claim 1; and
    a processing unit in which an electrical signal, output from the capacitive transducer due to an acoustic wave propagated from an object being incident upon the vibrating membrane, is used to acquire characteristic information relating to an inside of the object.

6. The object information acquiring apparatus according to claim 5, further comprising a transmission unit with which the vibrating membrane is vibrated by applying voltage to the pair of electrodes to cause transmission of an acoustic wave,
    wherein the acoustic wave is a reflection of the transmitted acoustic wave from an inside of the object.

7. The object information acquiring apparatus according to claim 5, further comprising a light source, wherein the acoustic wave is a photoacoustic wave generated from the object irradiated with light from the light source.

* * * * *